US010512586B1

United States Patent
Fung et al.

(10) Patent No.: US 10,512,586 B1
(45) Date of Patent: Dec. 24, 2019

(54) SYSTEM AND METHOD FOR VISION REHABILITATION THERAPY

(71) Applicant: Rayer Lavonne Lee, Hong Kong (HK)

(72) Inventors: Dan Lai Fung, Hong Kong (HK); Zhi Sheng Li, Beijing (CN); Rayer Lavonne Lee, Hong Kong (HK)

(73) Assignee: Rayer Lavonne Lee, Hong Kong (HK)

( * ) Notice: Subject to any disclaimer, the term of this patent is extended or adjusted under 35 U.S.C. 154(b) by 0 days.

(21) Appl. No.: 16/034,335

(22) Filed: Jul. 12, 2018

(51) Int. Cl.
| | |
|---|---|
| *A61H 5/00* | (2006.01) |
| *H01S 5/042* | (2006.01) |
| *H01S 5/00* | (2006.01) |
| *A61N 5/06* | (2006.01) |
| *A61H 39/04* | (2006.01) |
| *A61M 21/00* | (2006.01) |
| *A61N 5/067* | (2006.01) |
| *A61B 17/00* | (2006.01) |
| *A61B 18/20* | (2006.01) |

(52) U.S. Cl.
CPC ............. *A61H 5/00* (2013.01); *A61H 39/04* (2013.01); *A61M 21/00* (2013.01); *A61N 5/0613* (2013.01); *H01S 5/005* (2013.01); *H01S 5/042* (2013.01); *A61B 2017/00172* (2013.01); *A61B 2018/2055* (2013.01); *A61H 2201/10* (2013.01); *A61H 2201/5048* (2013.01); *A61M 2021/005* (2013.01); *A61N 2005/067* (2013.01); *A61N 2005/0651* (2013.01); *A61N 2005/0663* (2013.01)

(58) Field of Classification Search
CPC .... A51H 5/00; A51H 5/005; A61H 2205/024; A61N 5/0622
See application file for complete search history.

(56) References Cited

U.S. PATENT DOCUMENTS

| | | | | |
|---|---|---|---|---|
| 4,841,954 A | * | 6/1989 | Kalsi | A61H 23/0263 601/71 |
| 8,484,837 B2 | * | 7/2013 | Nickut | B23K 1/0016 29/840 |

(Continued)

FOREIGN PATENT DOCUMENTS

| | | |
|---|---|---|
| CN | 1351863 A | 6/2002 |
| CN | 103462787 A | 12/2013 |

(Continued)

OTHER PUBLICATIONS

Search Report of European Patent Application No. 18185659.2 dated May 20, 2019.

*Primary Examiner* — LaToya M Louis

(57) ABSTRACT

A system for vision rehabilitation therapy includes a controller, a laser generator for generating a laser beam with a cyclic frequency-varying laser pulse train having a frequency range of 10 Hz~35 Hz, and a light spot regulating device for forming a light spot with a diameter of about 20 mm and a laser power density of less than 1.5 mW/cm². A blade is disposed in front of the laser generator and shaped to block or unblock the laser beam as the blade rotates. A speed regulating motor is provided to regulate rotation speed of the blade through a drive circuit. A pair of virtual reality three-dimensional glasses is provided to generate a virtual reality three-dimensional green scenery, and a massage device is provided to massage acupoints around the eyes and on the head of a user.

15 Claims, 3 Drawing Sheets

(56) References Cited

U.S. PATENT DOCUMENTS

| | | | |
|---|---|---|---|
| 10,228,653 B2* | 3/2019 | Ochiai | G03H 1/0005 |
| 2006/0050229 A1* | 3/2006 | Farberov | A61B 3/117 |
| | | | 351/159.02 |
| 2009/0156886 A1* | 6/2009 | Burgio | A61B 5/224 |
| | | | 600/27 |
| 2009/0306555 A1* | 12/2009 | Goto | A61H 5/00 |
| | | | 601/15 |
| 2011/0112448 A1* | 5/2011 | Wu | A42B 3/145 |
| | | | 601/85 |
| 2011/0306999 A1* | 12/2011 | Lam | A61H 39/08 |
| | | | 606/189 |
| 2012/0323064 A1* | 12/2012 | Kim | A61K 9/0048 |
| | | | 600/15 |
| 2013/0066404 A1 | 3/2013 | Tapper et al. | |
| 2014/0171927 A1* | 6/2014 | Depfenhart | A61N 5/062 |
| | | | 606/5 |
| 2016/0045388 A1* | 2/2016 | Krenik | A61B 3/032 |
| | | | 351/201 |
| 2016/0067087 A1 | 3/2016 | Tedford et al. | |
| 2016/0302963 A1* | 10/2016 | Yang | A61H 23/00 |
| 2017/0156965 A1* | 6/2017 | Geisinger | G16H 50/20 |
| 2018/0132751 A1* | 5/2018 | Yarden | A61H 5/00 |
| 2018/0280718 A1* | 10/2018 | Tsubota | A61N 5/0613 |
| 2019/0091065 A1* | 3/2019 | Kelleher | A61F 9/00802 |
| 2019/0097722 A1* | 3/2019 | McLaurin | H04B 10/116 |

FOREIGN PATENT DOCUMENTS

| | | |
|---|---|---|
| CN | 103479472 B | 9/2015 |
| CN | 106214439 A | 12/2016 |
| CN | 205844640 U | 12/2016 |
| CN | 106309089 A | 1/2017 |

* cited by examiner

SYSTEM AND METHOD FOR VISION REHABILITATION THERAPY

FIELD OF THE TECHNOLOGY

The present disclosure relates to a system and method for vision rehabilitation therapy.

BACKGROUND

With the development of modern information technology, the use of electronic information products such as computers, mobile phones, televisions, and game consoles has become widespread. People's eye usage has increased dramatically. A large number of information processing products have been used by children to the elderly, especially students and technical workers. This results in excessive overuse of short-distance eyesight. Hence, asthenopia has become a normal condition, and the rate of amblyopia, myopia, blurred vision and other eye disorders is getting higher. The number of pupils wearing glasses is increasing. A main reason for abnormal eyesight is the reduction of activity of the eyeballs. The use of eyes to look at the screen for too long causes eye fatigue and reduction of regulating activity of the lens of the eye. Therefore, there is a need to develop a vision rehabilitation therapy system and method for therapeutic treatment of amblyopia, myopia, eye fatigue, blurry vision, and other visual disorder.

SUMMARY

According to one aspect, there is provided a system for vision rehabilitation therapy including:
  a controller;
  a laser source module coupled with the controller;
  a laser pulse train frequency regulation and control module coupled with the laser source module, the laser source module and the laser pulse train frequency regulation and control module being capable of generating a laser beam with a cyclic frequency-varying laser pulse train having a frequency range of 10 Hz~35 Hz; and
  a light spot regulating device coupled with the laser pulse train frequency regulation and control module, the light spot regulating device being capable of forming a light spot with a diameter of about 20 mm and a laser power density of less than 1.5 mW/cm².

In one embodiment, the laser source module and the laser pulse train frequency regulation and control module may include:
  a laser generator for generating the laser beam;
  a rotatable blade disposed in front of the laser generator, the blade being shaped to block or unblock the laser beam as the blade rotates;
  a speed regulating motor for rotating the blade and regulating speed of rotation of the blade; and
  a motor drive circuit coupled with a single-chip microcomputer which sends control signals to the speed regulating motor through the motor drive circuit.

In one embodiment, the laser beam is a red laser beam having a wavelength of 632.8 nm. The laser source module may include a semiconductor laser source.

The system for vision rehabilitation therapy may further include a pair of virtual reality three-dimensional glasses coupled with the controller, the pair of virtual reality three-dimensional glasses being provided with a virtual reality three-dimensional scenery device capable of generating a virtual reality three-dimensional green scenery environment in the pair of virtual reality three-dimensional glasses.

The system for vision rehabilitation therapy may further include a massage device coupled with the controller, the massage device being capable of massaging at least one acupoint around a user's eyes, and at least one vision-improving acupoint on the user's head.

The system for vision rehabilitation therapy may further include a voice prompting module coupled with the controller, the voice prompting module being capable of informing the user of the state of operation of the system.

The system for vision rehabilitation therapy may further include a product usage management module coupled with the controller, the product usage management module being capable of managing usage of the system.

The system for vision rehabilitation therapy may further include a product usage information storage coupled with the product usage management module, the product usage information storage being capable of storing information on duration of usage, number of usage, and user's information.

The system for vision rehabilitation therapy may further include a data communication interface coupled with the product usage information storage, the product usage management module, and the controller; the data communication interface being capable of facilitating data fetching, data communication and management.

According to another aspect, there is provided a method for vision rehabilitation therapy including:
  providing a controller, a laser source module coupled with the controller, a laser pulse train frequency regulation and control module coupled with the laser source module, and a light spot regulating device coupled with the laser pulse train frequency regulation and control module;
  generating, by the laser source module and the laser pulse train frequency regulation and control module, a laser beam with a cyclic frequency-varying laser pulse train having a frequency range of 10 Hz~35 Hz;
  forming, by the light spot regulating device, a light spot with a diameter of 20 mm and a laser power density of less than 1.5 mW/cm²; and
  carrying out a laser treatment by irradiating the laser beam at a user's eye for a period of time.

In one embodiment, the generating step may include:
  generating the laser beam by a laser generator;
  rotating, by a speed regulating motor, a rotatable blade disposed in front of the laser generator, the blade being shaped to block or unblock the laser beam as the blade rotates; and
  driving the speed regulating motor by a motor drive circuit according to control signals from a single-chip microcomputer.

In one embodiment, the laser pulse train has a number of cycles, each cycle lasting for one minute and having frequency increasing from 10 Hz to 35 Hz with increments of 1 Hz, and the laser pulse train lasts for 4~5 minutes.

In one embodiment, the laser power density is 0.1~0.5 mW/cm². The laser source module may include a semiconductor laser source.

The method for vision rehabilitation therapy may further include:
  mounting a pair of virtual reality three-dimensional glasses on a user's head;
  displaying, by a virtual reality three-dimensional scenery device, a virtual reality three-dimensional green scenery environment in the pair of virtual reality three-dimensional glasses; and prompting the user, by a voice prompting module, to gaze at the virtual reality three-dimensional green scenery environment for a period of time.

In one embodiment, the virtual reality three-dimensional green scenery environment is gradually changing.

The method for vision rehabilitation therapy may further include:
  mounting a pneumatic massage device on a user's head;
  prompting the user, by a voice prompting module, to close the eyes; and
  massaging, by the pneumatic massage device, at least one acupoint around the user's eyes for a period of time.

The method for vision rehabilitation therapy may further include:
  mounting a vibration massage device on a user's head; and
  massaging, by the vibration massage device, at least one vision-improving acupoint on the user's head for a period of time with a vibration massage frequency in the range of 5 Hz~25 Hz.

In one embodiment, the at least one acupoint on the user's head may include Baihui acupoint, Temple acupoint, and Fengchi acupoint.

Although the system and method for vision rehabilitation therapy are shown and described with respect to certain embodiments, it is obvious that equivalents and modifications will occur to others skilled in the art upon the reading and understanding of the specification. The system and method for vision rehabilitation therapy in the present application include all such equivalents and modifications, and is limited only by the scope of the appending claims.

BRIEF DESCRIPTION OF THE DRAWINGS

Specific embodiments of the system and method for vision rehabilitation therapy will now be described by way of example with reference to the accompanying drawings wherein.

DETAILED DESCRIPTION

Reference will now be made in detail to a preferred embodiment of the system and method for vision rehabilitation therapy, examples of which are also provided in the following description. Exemplary embodiments of the system and method for vision rehabilitation therapy are described in detail, although it will be apparent to those skilled in the relevant art that some features that are not particularly important to an understanding of the system and method for vision rehabilitation therapy may not be shown for the sake of clarity.

Furthermore, it should be understood that the system and method for vision rehabilitation therapy are not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure and appended claims.

Figure 1:
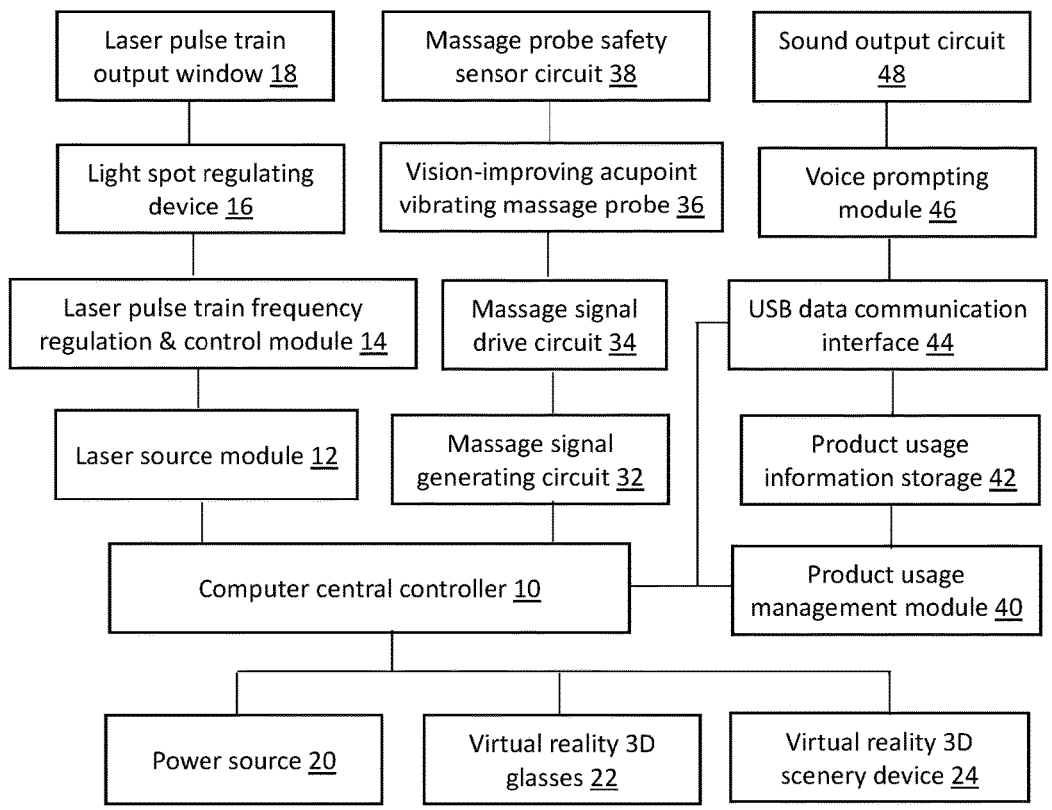
FIG. 1 is a block diagram of an embodiment of the vision rehabilitation therapy system.

FIG. 1 is a block diagram showing an embodiment of the vision rehabilitation therapy system of the present disclosure. The system for vision rehabilitation therapy may include a computer central controller 10, a laser source module 12 coupled with the controller 10, and a laser pulse train frequency regulation and control module 14 coupled with the laser source module 12. The laser source module 12 and the laser pulse train frequency regulation and control module 14 can generate a laser beam with a cyclic frequency-varying laser pulse train having a frequency range of 10 Hz~35 Hz. The laser source module 12 may include a semiconductor laser source, and the laser beam can be a red laser beam having a wavelength of 632.8 nm.

The system may also include a light spot regulating device 16 coupled with the laser pulse train frequency regulation and control module 14. The light spot regulating device 16 can form a light spot with a diameter of about 20 mm and a laser power density of less than 1.5 mW/cm$^2$. A power source 20 may be provided to supply power to the computer central controller 10 and other components and devices connected with the computer central controller 10.

Figure 2:
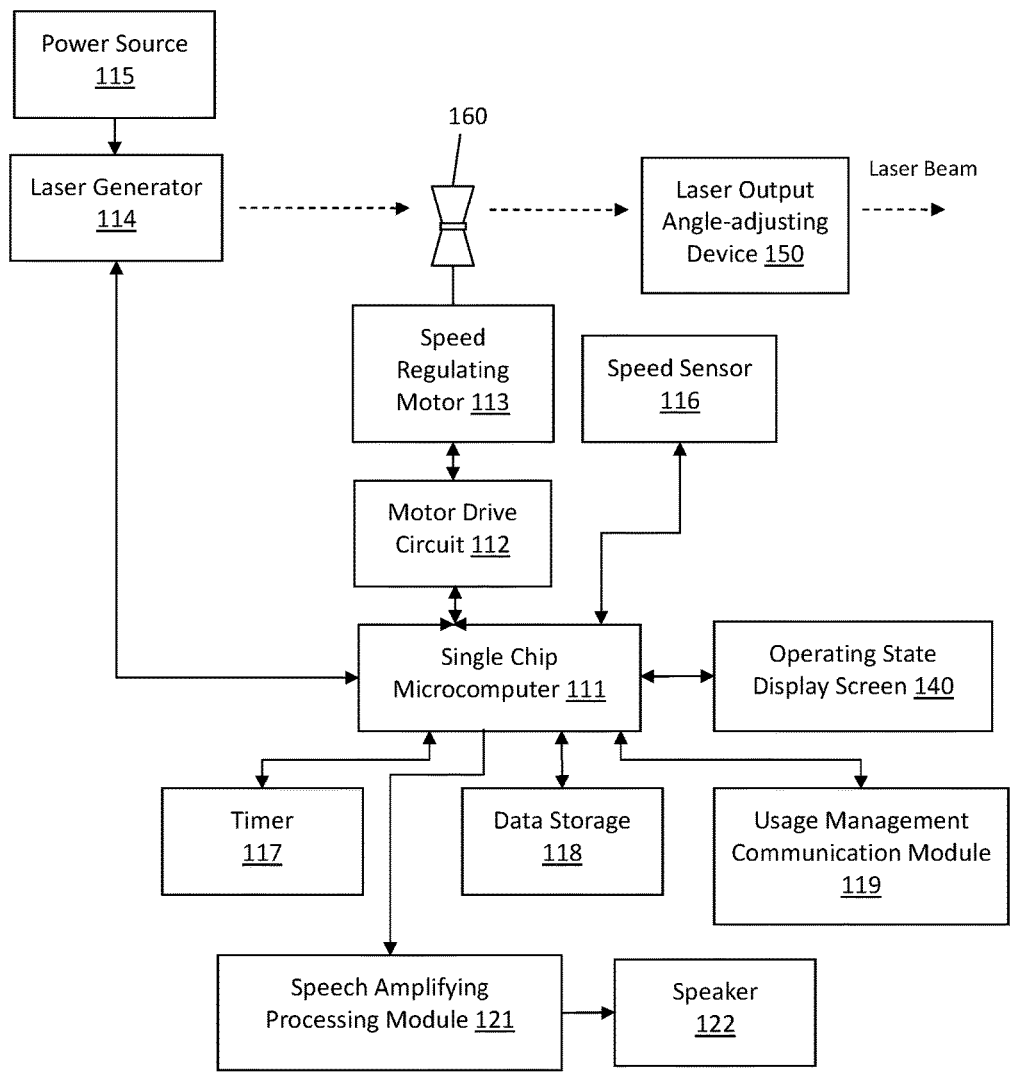
FIG. 2 is a block diagram showing the conversion of a continuous laser beam from a laser generator into a laser beam having a laser pulse train with a frequency of 10 Hz~35 Hz using a rotatable blade.

The laser source module 12 and the laser pulse train frequency regulation and control module 14 may include a laser generator 114 for generating the laser beam, a rotatable blade 160 disposed in front of the laser generator, as shown in FIG. 2. The blade may be shaped to block or unblock the laser beam as the blade rotates. A speed regulating motor 133 may be provided to rotate the blade and regulate the speed of rotation of the blade. A motor drive circuit 112 may be coupled with a single-chip microcomputer 111 for driving the speed regulating motor 113. The single-chip microcomputer 111 can send control signals to the speed regulating motor 113 through the motor drive circuit 112. The single-chip microcomputer 111 may be a part of the controller 10.

The system for vision rehabilitation therapy may further include a pair of virtual reality three-dimensional glasses 22 coupled with the controller 10. The pair of virtual reality three-dimensional glasses 22 may be provided with a virtual reality three-dimensional scenery device 24 capable of generating a virtual reality three-dimensional green scenery environment in the pair of virtual reality three-dimensional glasses 22.

The system for vision rehabilitation therapy may further include a massage device 32, 34, 36, 38 which may be coupled with the controller 10. The massage device can be used to massage the acupoints around a user's eyes as well as the vision-improving acupoints on the user's head, including the Baihui acupoint, the Temple acupoint, and the Fengchi acupoint.

The system for vision rehabilitation therapy may further include a voice prompting module 46 coupled with the controller 10. The voice prompting module 46 may be used to inform the user of the state of operation of the system.

The system for vision rehabilitation therapy may further include a product usage management module 40 coupled with the controller 10. The product usage management module 40 can be used to manage usage of the system.

The system for vision rehabilitation therapy may further include a product usage information storage 42 coupled with the product usage management module 40. The product usage information storage 42 can be used to store information such as duration of usage, number of usage, and user's information, etc.

The system for vision rehabilitation therapy may further include a data communication interface 44 coupled with the product usage information storage 42, the product usage management module 40, and the controller 10. The data communication interface 44 can be used to facilitate data fetching, data communication and management.

The present disclosure also discloses a method for vision rehabilitation therapy. First of all, the power is switched on, and the controller 10 enters a reset state. Then, the drive program begins to activate. The laser generator 114 generates a laser beam with a cyclic frequency-varying laser pulse train having a frequency range of 10 Hz~35 Hz. This is achieved by rotating, by the speed regulating motor 113, the rotatable blade 160 disposed in front of the laser generator 114. The blade 160 may be shaped to block or unblock the laser beam as the blade rotates. The speed regulating motor 113 may be driven by a motor drive circuit 112 according to control signals from the single-chip microcomputer 111. The laser beam is passed through the light spot regulating device 16 to form a light spot with a diameter of 20 mm and a laser power density of in the range of 0.1~0.5 mW/cm$^2$. The laser pulse train so generated may have a number of cycles, each cycle lasting for one minute and having frequency increasing from 10 Hz to 35 Hz with increments of 1 Hz, and the laser pulse train may last for 4~5 minutes. A laser treatment may be carried out by irradiating the pulsed laser beam at a user's eye for a period of time (e.g. 4~5 minutes).

After the laser treatment, an eye massage therapy may be carried out. The eye massage therapy may include the steps of: (a) mounting a massage device 32, 34, 36, 38, such as a pneumatic massage device, on a user's head; (b) prompting the user, by the voice prompting module 46, to close the eye; and (c) massaging the acupoints around the user's eyes for a period of time (e.g. 2~3 minutes).

After the eye massage therapy, an eye-relaxing therapy may be carried out. The eye-relaxing therapy may include the steps of: (a) mounting a pair of virtual reality three-dimensional glasses 22 on a user's head; (b) displaying, by a virtual reality three-dimensional scenery device 24, a built-in virtual reality three-dimensional green scenery environment in the pair of virtual reality three-dimensional glasses 22; and (c) prompting the user, by a voice prompting module 46, to gaze at the virtual reality three-dimensional green scenery environment for a period of time (e.g. 5 minutes). The virtual reality three-dimensional green scenery environment may be gradually changing during the eye-relaxing therapy.

During the eye-relaxing therapy, a head massage therapy may be carried out at the same time. The head massage therapy may include the steps of: (a) mounting a massage device, such as a vibration massage device, on a user's head; and (b) massaging the vision-improving acupoints on the user's head for a period of time (e.g. 5 minutes) with a vibration massage frequency in the range of 5 Hz~25 Hz.

Finally, a voice prompting indicates that the therapy is completed.

Vibration massage frequency of 5 Hz~25 Hz is a healthcare massage to acupuncture points around the eyes and on the head of a user. The massage device can massage 4 acupoints around one eye (8 acupoints for both eyes), as well as 2 Baihui acupoints, 3 Temple acupoints and 2 Fengchi acupoints on the head. Pneumatic massage may be used for massaging the acupoints around the user's eyes. Motor vibration massage may also be used for vibration massage of the vision-improving acupoints on the user's head. Through the drive circuit, the controller can control different parts of the massage device to carry out massage operations in accordance with the operating frequency set by the program. Acupoints on a human body are most sensitive to vibrating frequency in the range of 5 Hz~25 Hz. It can effectively activate the optic nerves and nerves in the brain and can effectively relieve eye fatigue.

The system and method for vision rehabilitation therapy are developed after many years of researches based on the current situation of amblyopia, nearsightedness, visual fatigue, and blurry vision. It uses automatic cyclic laser pulse train to irradiate and treat the retina of the eyes. Furthermore, it also uses virtual reality three-dimensional green scenery to recuperate the eyes, and massage device to massage the vision-improving acupoints. It combines ophthalmology and modern electronic information technology to realize comprehensive exercise and activation of the eyes. Thus, it can achieve the purpose of eye treatment and vision rehabilitation. It is an effective rehabilitation therapy for amblyopia, myopia, eye fatigue and blurry vision.

As described above, the vision rehabilitation therapy system and method may include the following seven parts:

a) A computer control circuit, which may include a single-chip microcomputer, a voice prompting module, a drive circuit and a drive software program. It is a control center of the system.

b) A laser pulse train generating circuit, which may include a semiconductor laser source, and a laser pulse train generating and driving circuit.

c) A vibration massage circuit, which may include a vibration massage device for massaging acupoints around the eyes and vision-improving acupoints on the head, and a drive circuit.

d) A virtual reality green scenery display circuit, which may include scenery pictures, a light illumination circuit, and a three-dimensional space establishing circuit.

e) A virtual reality three-dimensional glasses, which may include a position-adjusting mechanism for adjusting the interpupillary distance and object distance of the lenses and glasses.

f) A data communication interface, which may include a product usage management module, and a USB serial data communication interface.

g) A power source circuit and a housing.

The vision rehabilitation therapy system and method may have the functions of (a) providing laser irradiation treatment of the eyes with cyclic frequency-varying laser pulse train, (b) offering vibration massage of acupoints around the eyes and vision-improving acupoints on the head, (c) generating a virtual reality three-dimensional green scenery relaxing therapy for the eyes, (d) providing voice prompting throughout the entire operating procedures, and (e) managing product usage information and communication.

The vision rehabilitation therapy is suitable for (a) people with amblyopia and myopia, (b) people with asthenopia and excess eye usage, and (c) presbyopia prevention and rehabilitation training for the elderly.

The main performance parameters of the vision rehabilitation therapy system and method are as follows:

a) Operating laser peak wavelength: 632.8 nm
b) Laser output average power: 0.7 mW~2 mW
c) Laser power density at treatment site: 0.1~0.5 mW/cm$^2$
d) Laser mode: multimode He—Ne laser
e) Laser pulse train frequency: 10 Hz~35 Hz
f) Laser pulse train frequency changing rate: 0.42 Hz/s
g) Vibration massage frequency: 5 Hz~25 Hz The operating laser peak wavelength may be 632.8 nm. The vibration rehabilitation therapy system and method may utilize a pure red light wave with a wavelength of 632.8 nm.

It is the most sensitive wavelength for the retina in the macular region of the eyes. It has the following effects on eye rehabilitation for amblyopia and myopia:

a) irradiation and stimulation for a short period of time (around 5 minutes) can accelerate the synthesis of ciliary muscle tissue proteins in the eyes, increase the content of carbohydrate source, and increase the activity of ribonucleic acid. The treatment may be performed once every day for about 5 minutes. The accumulated effect begins to gradually increase on the third or fourth day, and usually reaches its peak in 10~15 days; and b) Pyramidal cells of the eyes are very sensitive to red light wave and have a high absorption rate. It can activate and enhance sensitometric function of the pyramidal cells. The thermal effects and biochemical effects on the retina can make the blood vessels of the retina and choroid expand, and therefore improve blood circulation.

The laser output average power may be in the range of 0.7 mW~2 mW. Laser output average power refers to the output average power of a selected laser device. However, it is not the power that reaches the treatment site of the eyes. The light spot of the laser output of the laser device must be expanded by a beam expander before irradiating on the eyes. Thus, the laser average power that is received by the eyes is much smaller than the laser power output from the laser device, and the measured value is less than 0.5 mW.

The laser power density at the treatment site may be in the range of 0.1~0.5 mW/cm$^2$. The laser power density at the treatment site refers to the density of the laser power irradiated on the eyeballs, which may be between 0.1~0.5 mW/cm$^2$. This density meets the requirement of Class 1 laser (safe laser without harm). After beam expansion by a beam expander, the diameter of light spot at the treatment site can be expanded to 3 cm, and the laser power density may be set at a range of 0.1~0.5 mW/cm$^2$. This can meet the irradiation treatment requirement and leave a large margin for the safety of the eyes.

The laser pulse train frequency may be in the range of 10 Hz~35 Hz. Converting a continuous laser beam into a laser pulse train with a frequency of 10 Hz~35 Hz is the main technical feature of the vision rehabilitation therapy system and method of the present disclosure. It is the result of long-term research and clinical practice by the inventors. After theoretic comparison, the inventors find out that frequency-varying laser beam can more effectively stimulate the excitation of visual nerves than constant-light laser beam. The laser beam can be converted into a laser pulse train with a frequency of 15 Hz~25 Hz. Through the setting up of a constant-light group and a frequency-varying group, irradiation test was performed on mice. It is found that after 3 minutes of laser irradiation, there was no significant difference between the activity of mice in the constant-light group and the frequency-varying group. After 5~10 minutes, there was a significant difference between the mice in the constant-light group and the frequency-varying group. The activity of mice in the constant-light group was significantly lower than that in the frequency-varying group. The excitement of mice in the frequency-varying group had increased significantly. Under the condition that the laser irradiation density is less than 0.5 mW (comply with safe density of Class 1 laser), ten amblyopic patients with similar amblyopia levels in the constant-light group and the frequency-varying group were arranged to perform eye irradiation treatments. Each irradiation treatment was performed for 4 minutes. After 10 treatments, the result was that the average vision improving rate of the constant-light group was 0.03 diopter/time; whereas the average vision improving rate of the frequency-varying group was 0.052 diopter/time. It can be seen that the vision improving rate of the frequency-varying group was significantly higher than that of the constant-light group. This shows that low-frequency, varying frequency of pure red light laser can significantly improve the effect of amblyopia treatment.

Frequency range 10 Hz~35 Hz is the most sensitive frequency range for the eyes. The frequency range is combined with low-power pure red light to generate frequency-varying laser pulse train with a frequency range of 10 Hz~35 Hz. This is used for the rehabilitation of patients with amblyopia and is the main technical feature of the vision rehabilitation therapy system and method of the present disclosure. At the present time, no similar products are found on the market.

As mentioned, FIG. 2 shows the conversion of a continuous laser beam from a laser generator into a laser beam having a laser pulse train with a frequency of 10 Hz~35 Hz. The system may include a single-chip microcomputer 111, a drive circuit 112, a speed regulating motor 113, a rotatable blade 160, a laser generator 114 and a power source 115. The single-chip microcomputer 111 can send control signals to the speed regulating motor 113 through the drive circuit 112. The speed regulating motor 113 can be a stepper motor. The laser generator 114 can be a He—Ne laser generator. The power source 115 can be an external 1500V power source.

The speed regulating motor 113 can drive the rotatable blade 160 to rotate. For each revolution, the laser beam is blocked and unblocked by the blade once. The ratio of the times the laser beam is blocked and unblocked can be achieved by changing the shape of the blade. This results in the conversion of a continuous laser beam to a laser pulse train with a frequency range of 10 Hz~35 Hz. For example, the laser pulse train may have a number of cycles. Each cycle may last for one minute with frequency increasing from 10 Hz to 35 Hz with increments of 1 Hz (i.e. 10 Hz, 11 Hz, 12 Hz, . . . 35 Hz). The duration of a single frequency may be 0.42 second. After one minute, frequency goes back to 10 Hz and starts the next cycle. The duration of the entire laser pulse train may last for 4~5 minutes.

The system may further include speed sensor 116, timer 117, data storage 118, usage management communication module 119, speech amplifying and processing module 121 and speaker 122. The timer 117 may be used to monitor or control frequency and time of each treatment. The speech amplifying and processing module 121 and speaker 122 may be used to generate voice prompting or play soft music during treatment.

Figure 3:
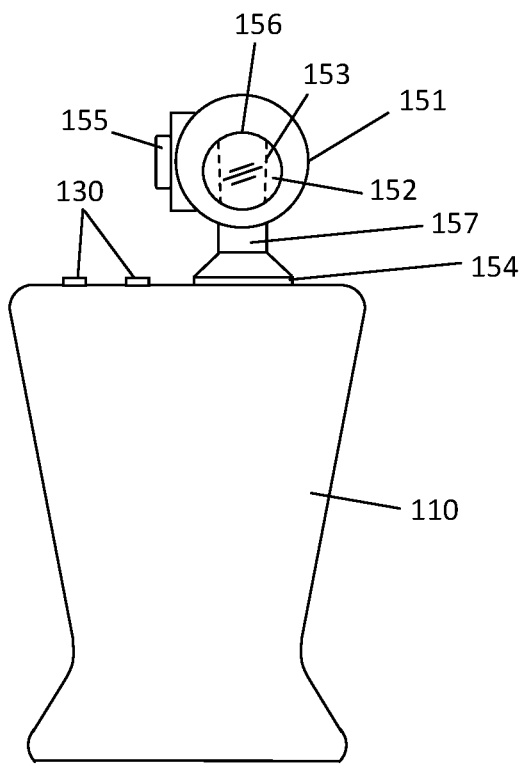
FIG. 3 is a front view of an embodiment of a laser output angle-adjusting device.
Figure 4:
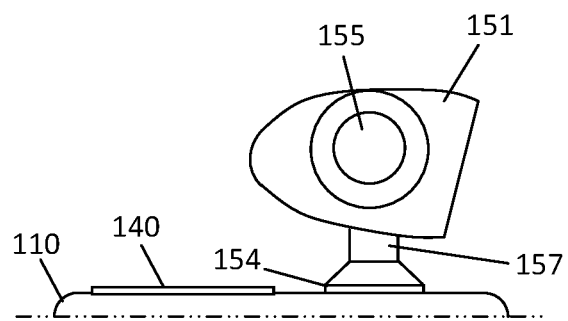
FIG. 4 is a side view of the laser output angle-adjusting device of FIG. 3.

FIGS. 3-4 show an embodiment of a laser output angle-adjusting device. The vision rehabilitation therapy system of the present disclosure may include a laser output angle-adjusting device 150 for adjusting the angle of laser output. The laser output angle-adjusting device 150 may include a base 110, and a casing 151 mounted on the base through a pillar 157 and a bearing housing 154. A reflector 153 may be provided in the casing 151 for reflecting laser beam towards a glass 152 in an opening 156 of the casing 151. The glass 152 may have a filter for filtering out red light. A knob 155 may be provided on the casing 151 to adjust the angle of the casing. Buttons 130 and display screen 140 may be provided on top of the base.

The assessment of safety of the automatic cyclic laser pulse train for a human is based on "GB 7247.1-2012 Safety of Laser Products—Part 1: Equipment Classification, Requirements and User Guide" (IEC60825-1:2007); German version EN60825-1:2007.

The classification of the laser of the vision rehabilitation therapy system is a Class 1 laser product. The laser has a laser wavelength is 635 nm. Treatment time can be set at 300 seconds. Treatment can be carried out once per day. The safety analysis and assessment are shown in the following table:

| Safety Assessment Analysis Table of Vision Rehabilitation Therapy System | | | |
|---|---|---|---|
| Safety Content | GB7247.1-2012 Requirement | Vision Rehabilitation Therapy System | Safety Compliance |
| Laser Product Classification | Class 1 Laser Product | Class 1 Laser Product | Comply |
| Laser Wavelength | 500 nm~700 nm | 635 nm | Comply with wavelength range requirement |
| Laser Emission Duration | 100 S~1000 S | 300 S | Comply with duration range requirement |
| Laser Power | ≤0.39 mW | 0.05 mW~0.1 mW | Comply with power range requirement |
| Irradiation Energy Value on Retina | Hazard limit value on retina 50.46 mJ (Calculate standard maximum value according to treatment duration of 300 S) | 25.23 mJ (Effective pulse time of laser pulse train is ½ of treatment time) | Retina light energy irradiation value of the vision rehabilitation therapy system is less than maximum value of standard Class 1 laser product. There is a 50% safety margin. |
| Safety Assessment Conclusion | All performance indicators of the vision rehabilitation therapy system comply with GB7247.1-2012 standard requirements. It has sufficient safety margin and is safe for vision rehabilitation therapy. | | |

Long-term use of virtual reality glasses can cause eye fatigue. In particular, watching video on mobile phones through virtual reality will further increase eye fatigue. This is because the light is direct light. It is the light that is directly emitted from the light source. Since brightness of the light is strong, it is easy to cause eye fatigue. This is similar to the fact that we cannot look directly at the sun, but we can look directly at the moon light. It is because moon light is reflected light, and its light intensity is low. Therefore, there is no harm to the eyes, and it will not cause eye fatigue.

The light path of the light source of the virtual reality three-dimensional green scenery environment display device of the vision rehabilitation therapy system is in the same direction as the eye's visual direction. The light does not irradiate towards the eyes. The green scenery at the background appears only under illumination of the light source. As mentioned, the green scenery background is produced by reflected light. The effect of this reflected light is similar to that of the moon light. Looking at such a green scenery background will be comfortable and relaxing and will not cause eye fatigue.

While the system and method for vision rehabilitation therapy have been shown and described with particular references to a number of preferred embodiments thereof, it should be noted that various other changes or modifications may be made without departing from the scope of the appended claims.

What is claimed is:

1. A system for vision rehabilitation therapy, comprising:
a controller;
a laser source module coupled with the controller;
a laser pulse train frequency regulation and control module coupled with the laser source module, the laser source module and the laser pulse train frequency regulation and control module being capable of generating a laser beam with a cyclic frequency-varying laser pulse train having a frequency range of 10 Hz-35 Hz;
a light spot regulating device coupled with the laser pulse train frequency regulation and control module, the light spot regulating device being capable of forming a light spot with a diameter of about 20 mm and a laser power density of less than 1.5 mW/cm$^2$; and a massage device coupled with the controller, the massage device configured for massaging at least one acupoint around a user's eyes, and at least one vision-improving acupoint on the user's head during use;
wherein the laser source module and the laser pulse train frequency regulation and control module comprise:
a laser generator for generating the laser beam;
a rotatable blade disposed in front of the laser generator, the blade being shaped to block or unblock the laser beam as the blade rotates;
a speed regulating motor for rotating the blade and regulating speed of rotation of the blade; and
a motor drive circuit coupled with a single-chip microcomputer which sends control signals to the speed regulating motor through the motor drive circuit.

2. The system for vision rehabilitation therapy as claimed in claim 1, wherein the laser beam is a red laser beam having a wavelength of 632.8 nm.

3. The system for vision rehabilitation therapy as claimed in claim 1, wherein the laser source module comprises a semiconductor laser source.

4. The system for vision rehabilitation therapy as claimed in claim 1, further comprising a pair of virtual reality three-dimensional glasses coupled with the controller, the pair of virtual reality three-dimensional glasses being provided with a virtual reality three-dimensional scenery device capable of generating a virtual reality three-dimensional green scenery environment in the pair of virtual reality three-dimensional glasses.

5. The system for vision rehabilitation therapy as claimed in claim 1, further comprising a voice prompting module coupled with the controller, the voice prompting module being capable of informing the user of the state of operation of the system.

6. The system for vision rehabilitation therapy as claimed in claim 1, further comprising a data communication interface coupled with the controller; the data communication interface being capable of facilitating data fetching, data communication and management.

7. A method for vision rehabilitation therapy comprising:
provide a controller, a laser source module coupled with the controller, a laser pulse train frequency regulation and control module coupled with the laser source module, and a light spot regulating device coupled with the laser pulse train frequency regulation and control module;
generating, by the laser source module and the laser pulse train frequency regulation and control module, a laser beam with a cyclic frequency-varying laser pulse train having a frequency range of 10 Hz-35 Hz;
forming, by the light spot regulating device, a light spot with a diameter of 20 mm and a laser power density of less than 1.5 mW/cm$^2$;
carrying out a laser treatment by irradiating the laser beam at a user's eye for a period of time;
and massaging, by a massage device coupled with the controller, at least one acupoint around a user's eyes, and at least one vision-improving acupoint on the user's head;
wherein the generating step comprises:
generating the laser beam by a laser generator;
rotating, by a speed regulating motor, a rotatable blade disposed in front of the laser generator, the blade being shaped to block or unblock the laser beam as the blade rotates; and driving the speed regulating motor by a motor drive circuit according to control signals from a single-chip microcomputer.

8. The method for vision rehabilitation therapy as claimed in claim 7, wherein the laser source module comprises a semiconductor laser source.

9. The method for vision rehabilitation therapy as claimed in claim 7, wherein the laser pulse train has a number of cycles, each cycle lasting for one minute and having frequency increasing from 10 Hz to 35 Hz with increments of 1 Hz, and the laser pulse train lasts for 4~5 minutes.

10. The method for vision rehabilitation therapy as claimed in claim 7, wherein the laser power density is 0.1~0.5 mW/cm$^2$.

11. The method for vision rehabilitation therapy as claimed in claim 7, further comprising:
mounting a pair of virtual reality three-dimensional glasses on a user's head;
displaying, by a virtual reality three-dimensional scenery device, a virtual reality three-dimensional green scenery environment in the pair of virtual reality three-dimensional glasses; and
prompting the user, by a voice prompting module, to gaze at the virtual reality three-dimensional green scenery environment for a period of time.

12. The method for vision rehabilitation therapy as claimed in claim 11, wherein the virtual reality three-dimensional green scenery environment is gradually changing.

13. The method for vision rehabilitation therapy as claimed in claim 7, further comprising:
wherein the massage device comprises a pneumatic massage device;
mounting the pneumatic massage device on a user's head; prompting the user, by a voice prompting module, to close the eyes; and massaging, by the pneumatic massage device, at least one acupoint around the user's eyes for a period of time.

14. The method for vision rehabilitation therapy as claimed in claim 7, further comprising:
wherein the massage device comprises a vibration massage device;
mounting the vibration massage device on a user's head; and
massaging, by the vibration massage device, at least one vision-improving acupoint on the user's head for a period of time with a vibration massage frequency in the range of 5 Hz-25 Hz.

15. The method for vision rehabilitation therapy as claimed in claim 14, wherein the at least one acupoint on the user's head comprises Baihui acupoint, Temple acupoint, and Fengchi acupoint.

\* \* \* \* \*